United States Patent [19]

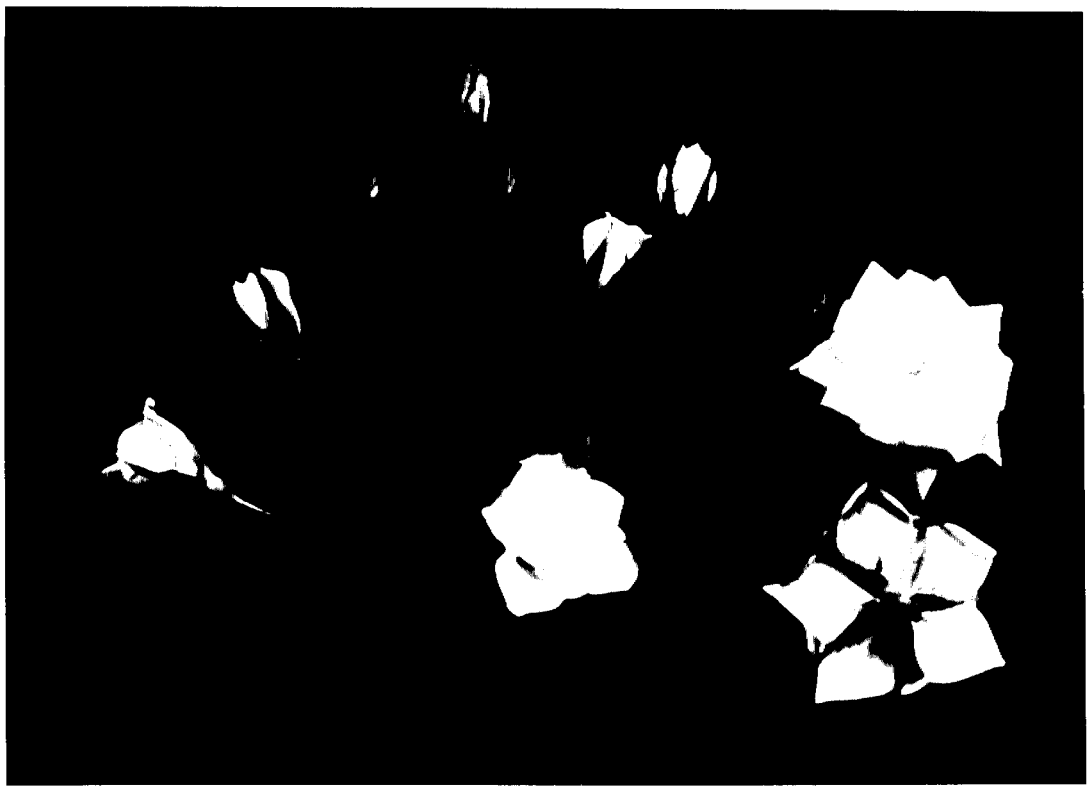

Moore

[11] Patent Number: Plant 5,742

[45] Date of Patent: May 13, 1986

[54] MINIATURE ROSE PLANT/MORLYN

[75] Inventor: Ralph S. Moore, Visalia, Calif.

[73] Assignee: Sequoia Nursery, Visalia, Calif.

[21] Appl. No.: 574,578

[22] Filed: Jan. 27, 1984

[51] Int. Cl.[4] ..... A01H 5/00

[52] U.S. Cl. ..... Plt./8

[58] Field of Search ..... Plt./8

*Primary Examiner*—Robert E. Bagwill

[57] ABSTRACT

This invention relates to a new and distinct variety of miniature rose plant primarly identified by small yellow buds and flowers which are abundantly produced on a much branched compact plant.

1 Drawing Figure

The present invention relates to a new and distinct variety of hardy, dwarf, bush type rose plant of the miniature class; the variety being primarily characterized—as to novelty—by clear yellow buds and flowers which in general color effect are similar to Rise N'Shine (miniature—U.S. Plant Pat. No. 4,231).

The variety is further characterized by:

An abundance of bloom, with flowers borne singly or several to the stem in loose clusters.

Light but sweet fragrance.

A plant which is vigorous, of compact rounded to slightly spreading shape and with small semi-glossy to matt foliage with pointed leaflets; the buds and flowers being similar in form to Rise N'Shine (miniature—U.S. Plant Pat. No. 4,231) but smaller in size and the flowers being less double.

The plant, which has a normal height of about 10 inches, can easily be maintained at lesser height by occasional trimming.

A plant which grows and blooms satisfactorily both in greenhouse and outdoors; is good for growing in pots; and provides excellent garden decoration as well as cut flowers.

The present variety of miniature rose was originated by me at my nursery located at Visalia, Calif., under conditions of careful control and observation as a cross between Ellen Poulson (Polyantha—not patented) as the seed parent and Yellow Jewel (miniature—U.S. Plant Pat. No. 3,627) as the pollen parent.

Subsequent to origination of the variety I successfully asexually reproduced it, in my nursery located as aforesaid, by budding as well as by cuttings; the reproductions having run true in all respects.

The color photograph illustrates the variety, including foliage, buds and flowers.

Referring now specifically to the new and distinct variety of miniature rose plant, the following is a detailed description thereof in outline; all major color plate identifications being by reference to the British Colour Council Horticultural Colour Chart, except where common terms of color definitions are employed.

Type: Hardy, dwarf; bushy rounded; upright to slightly spreading; seedling; greenhouse; outdoors; cut flowers; garden decoration; potted plant.

Class: Miniature. Variety identification: MORlyn — Commercial synonym: Lynne Gold.

Flowers: Continuity; continuous — repeat bloom all season.

*Fragrance.*—Sweet tea rose.

Flowers borne: Singly and several together (3 to 5 sometimes more) on tips of main shoots and on shorter lateral shoots.

Quantity of bloom: Abundant both outside and in greenhouse.

Bud:

*Peduncle.*—Medium to short length; slender but sturdy; erect; medium green, sometimes tinted bronze (outdoors); Hairs — Few — or none.

*Before calyx breaks; size.*—Small. Form long; pointed with several foliaceous appendages and few or no hairs on surface of bud; with foliaceous parts extending beyond the tip of the bud equal to one-half or less of its length.

*Color.*—Medium green, occasionally tinted with bronze (outdoors).

*As calyx breaks, color.*—Clear yellow/ near Saffron Yellow 7/2. Opening: opens well in all weather; color near Indian Yellow 6/2 (at certain times due to weather, the yellow color is slightly modified with a bit of red); size — small.

Bloom:

*Size when fully open.*—Small, averaging about 25–28 mm.

*Petalage.*—Double — 18–20 petals, arranged regularly plus sometimes several small petaloids.

*Form.*—Flat to slightly rounded at first, becoming more open in the center, with petals rolled loosely outward, and later at maturity, open with petals folded at tips to give a pointed effect. Fully open flowers usually show stamens.

Petals: Fairly thick; satiny on inside and on outside surface.

*Shape.*—Outside petals, broad lanceolate with rounded or small acute tip; intermediate — broad lanceolate with rounded tip.

*Inside.*—Lanceolate with rounded tip.

Color: Newly opened flower from a plant grown in plastic greenhouse (October 1983), Visalia, Calif.

*Outside petal.*—Outside surface — near Indian Yellow 6/2 to Saffron Yellow 7/2; inside surface — near Indian Yellow 6/2 to near Saffron Yellow 7/2 at base.

*Intermediate petal.*—Outside surface — similar to outside petal. Inside surface — similar to outside petal.

*Inner petal.*—Outside surface — same as intermediate petal; Inside surface — Same as intermediate petal. General color effect newly opened flowers — Clear yellow. Three days open — Color similar to newly opened flowers but lighter color. Behavior — Due to cultural factors such as soil fertility, light intensity, day length, etc., the intensity of the yellow color may vary. The buds and fresh opened flowers often being deeper yellow — Near Saffron Yellow 7/2 (especially in cooler weather). Spent petals drop off. Flower longevity (October 1983) — Plant in pot 5–7 days or longer. Cut flowers at living room temperature 4–5 days or longer.

Reproductive organs:

*Stamens.*—Abundant, arranged regularly about pistil.

*Filaments.*—Varying length, yellow.

*Anthers.*—Well formed; yellow.

*Pollen.*—Little or none.

*Pistils.*—Average number.

*Styles.*—Yellow.

*Ovaries.*—All enclosed in calyx.

*Hips.*—None.

*Sepals.*—Permanent; spear shaped; recurved.

*Seed.*—None.

Foliage:

*Leaves.*—Compound of five (sometimes three or seven) leaflets; abundant; very small; semi-glossy to matt.

*Leaflets.*—Shape: broad, lanceolate; apex acute; base rounded or rounded acute. Margin serrate. Color — Medium green; new growth — normal (medium) green, sometimes reddish (outdoors). Rachis: Medium strength; upper side may have a few very small short hairs, grooved; underside; few or no thorns with few or no tiny prickles. Stipules: Medium long; narrow to medium width, with numerous hair-like serrations along margins; medium length narrow points which turn out usually at about 45 degrees.

Growth:

*Habit.*—Dwarf; bushy; upright to spreading; much branched.

*Growth.*—Free vigorous; internodes short.

*Canes.*—Medium; slender; sturdy.

*Main stems.*—Color: medium green.

*Thorns.*—Few to none — If present, nearly straight; color; brown. Prickles — None. Hairs — None.

*Branches.*—Color: Light to medium green. Thorns: Few to none.

The miniature rose plant and its flowers as herein described may vary in slight detail due to climatic, soil and cultural conditions under which the variety may be grown; the present description being of the variety as grown at Visalia, Calif.

The following is claimed:

1. A new and distinct variety of miniature rose plant of hardy, dwarf, bushy, upright to spreading, much branched habit, substantially as illustrated and described, characterized by buds and flowers which are generally of a clear yellow color, with buds and flowers being similar in shape to Rise N'Shine (miniature—U.S. Plant Pat. No. 4,231) but smaller in size and with less petals; and further characterized by a plant similar to Cinderella (miniature—U.S. Plant Pat. No. 1,051—expired) which is vigorous and compact, the shoots and branches having short internodes, said plant being easy to propagate from cuttings and having an abundance of semi-glossy to matt foliage, with flowers borne singly or several to the stem in loose clusters.

* * * * *